(12) United States Patent
Peterson

(10) Patent No.: US 6,780,012 B1
(45) Date of Patent: Aug. 24, 2004

(54) ARTICLE WITH LASER ENGRAVED IDENTIFICATION MARK

(75) Inventor: Dale D. Peterson, Maplewood, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 09/466,947

(22) Filed: Dec. 20, 1999

(51) Int. Cl.$^7$ .............................. A61C 5/04; A61C 3/00; B29C 35/08

(52) U.S. Cl. ...................... 433/90; 433/23; 219/121.68; 264/400

(58) Field of Search ................ 433/23, 90; 219/121.65, 219/121.66, 121.68, 121.69; 430/346; 283/85; 493/961; 264/400; 428/195

(56) References Cited

U.S. PATENT DOCUMENTS

| | | | |
|---|---|---|---|
| 3,931,458 A | | 1/1976 | Dini |
| 4,120,090 A | * | 10/1978 | Kesling |
| 4,195,046 A | | 3/1980 | Kesling |
| 4,304,981 A | | 12/1981 | Gappa |
| 4,323,317 A | * | 4/1982 | Hasegawa |
| 4,323,755 A | * | 4/1982 | Nierenberg |
| 4,439,154 A | | 3/1984 | Mayclin |
| 4,523,777 A | * | 6/1985 | Holbein et al. ................ 283/67 |
| 4,579,754 A | * | 4/1986 | Maurer et al. ................. 428/29 |
| 4,626,209 A | | 12/1986 | Tsai et al. |
| 4,663,518 A | * | 5/1987 | Borror et al. ................ 235/487 |
| 4,693,567 A | | 9/1987 | Ozaki |
| 4,861,620 A | * | 8/1989 | Azuma et al. |
| 4,900,252 A | | 2/1990 | Liefke et al. |
| 5,044,955 A | | 9/1991 | Jagmin |
| 5,061,341 A | * | 10/1991 | Kildal et al. |
| 5,100,320 A | | 3/1992 | Martin et al. |
| 5,195,663 A | | 3/1993 | Martin et al. |
| 5,238,402 A | | 8/1993 | Rohlcke et al. |
| 5,298,922 A | * | 3/1994 | Merkle et al. ................ 346/1.1 |
| 5,322,436 A | * | 6/1994 | Horng et al. .................. 433/23 |
| 5,326,259 A | | 7/1994 | Rohlcke et al. |
| 5,446,338 A | * | 8/1995 | Lee |
| 5,556,276 A | | 9/1996 | Roman et al. |
| 5,624,260 A | | 4/1997 | Wilcox et al. |
| 5,626,966 A | * | 5/1997 | Kulper et al. |
| 5,662,472 A | * | 9/1997 | Grutzner ....................... 433/90 |
| 5,688,573 A | * | 11/1997 | Goeb et al. ................ 428/40.1 |
| 5,824,397 A | | 10/1998 | Koops et al. |

(List continued on next page.)

FOREIGN PATENT DOCUMENTS

| | | |
|---|---|---|
| DE | 19758083 | 1/1999 |
| EP | 0085484 | 8/1983 |

OTHER PUBLICATIONS

Dentaurum Advertisement in British Journal of Orthodontics, vol. 19, No. 3, Aug. 1992.
Dentaurum Laser I.D. System Advertisement, undated.
Mark Takarabe, "Precision Sensing With Lasers", Machine Design, Jul. 23, 1992, pp. 62, 64, 66.

Primary Examiner—Ralph A. Lewis
(74) Attorney, Agent, or Firm—James D. Christoff

(57) ABSTRACT

An article includes a polymer coating extending over a region of an exterior surface of the article and a laser engraved identification mark formed within the coating. The polymer coating has a color that contrasts with the color of the exterior surface, resulting in an identification that is distinct and easy to read. Optionally, the laser engraved identification mark represents species data pertaining to the article while the polymer coating can be used to create a second identification mark that represents genus data pertaining to the article, consequently facilitating visual differentiation of various articles by the consumer while also reducing manufacturing costs.

26 Claims, 1 Drawing Sheet

U.S. PATENT DOCUMENTS 5,855,969 A * 1/1999 Robertson
5,893,714 A * 4/1999 Arnold et al. ............... 433/90
5,958,528 A * 9/1999 Bernecker
6,007,929 A * 12/1999 Robertson et al.
6,054,090 A * 4/2000 Duis et al.
6,169,266 B1 * 1/2001 Hughes
6,261,348 B1 * 7/2001 Kwan et al.
6,433,302 B1 * 8/2002 Miller et al.

* cited by examiner

ARTICLE WITH LASER ENGRAVED IDENTIFICATION MARK

BACKGROUND OF THE INVENTION

1. Field of the Invention

This invention relates to an article and a method for making an article having one or more identification marks that function to identify information about the article, such as color, size, catalog number and the like. More particularly, the present invention is concerned with an article and a method for making an article having a laser engraved identification mark that is created by the use of a polymer coating applied to an exterior surface of the article.

2. Description of the Related Art

Laser engraving apparatus is in widespread use for marking or engraving a variety of articles. Common examples of laser engraved articles include trophies, signs, sporting goods and awards. Other laser engraved articles include product containers, musical instruments and woodcrafts.

Product containers often bear a number of identification marks that serve various purposes. Product containers commonly include at least the name of the product as well as the name of the manufacturer or seller of the product. If the nature of the product is not readily apparent, the container may also include identification marks written as text that describe in generic terms the type of product within the container.

In many instances, product containers also include a number of additional identification marks that serve other purposes. For example, the container may have marks that describe the color, shape, size, weight or volume of the product. It is also common for product containers to bear marks that identify the manufacturer's or seller's address, or country of origin of the product.

Many product containers also include additional identification marks that convey other information as well. For example, identification marks on product containers may include serial numbers or batch or lot codes that help identify, among other things, more detailed information to the manufacturer regarding the manufacturing process for the particular product within the container. Furthermore, identification marks on product containers may include letters or numbers that serve as catalog or product numbers for the product.

In the past, identification marks have frequently been applied to product containers using ink printing technology of one sort or another. In some instances, ink markings are applied to a label such as a label made from a section of paper or plastic film having an adhesive coating on its back side. The label is often applied to the container after the label is marked.

In other instances, ink printing technology is used to apply an ink identification mark directly on an exterior surface of the container. In that instance, the color of the ink is often selected to contrast with the color of the exterior surface of the container in order to enhance the visibility of the resulting identification mark. The identification mark may be formed as a positive image of the ink (i.e., where the ink creates letters, symbols or other indicia for identification) or as a negative image (such that the lack of ink, and hence the underlying exterior surface of the container, creates the letters, numbers or other indicia).

However, certain problems have long been associated with ink printing. For example, the operator must ensure that a sufficient quantity of fresh ink is available at all times. Also, the operator must ensure that the ink has properly hardened or cured after application so that the mark is not smudged or otherwise harmed during subsequent handling. Moreover, and particularly with ink pad printing technology, there is often a certain amount of labor, time and expense associated with efforts to switch from one identification mark to another.

In recent years, laser technology has been used to engrave product identification marks directly on product containers. Laser engraving technology presents an important advantage over ink printing technology, in that the laser engraving apparatus enables the operator to easily switch from one identification mark to another. For example, the laser engraving apparatus may include a controller that directs movement of the laser beam. In that instance, changing the identification mark is carried out by simply changing a set of computer instructions used by the controller to determine the path of the beam.

However, laser engraved identification marks on product containers are sometimes difficult to see. The ease of visibility of the mark depends on many factors, including the width of the mark and the color of the underlying container surface. The operator must also exercise caution to ensure that the energy of the beam on the surface of the container is not sufficient to burn through or otherwise unduly weaken the container, so that the strength of the container is not significantly impaired.

Laser engraved identification marks have also been used on other dental articles. For example, U.S. Pat. No. 5,322,436 describes an orthodontic band that has a laser engraved identification mark on an exterior surface. The identification mark described in that patent has a white, frosty appearance that is aesthetic and easy to read.

Known identification marks, including the marks described above, are somewhat satisfactory and are in widespread use. However, there is a continuing need to improve the state of the art. In particular, it would be desirable to provide an identification mark that is easy to read, and yet is also durable and relatively inexpensive to manufacture, even when a relatively large amount of information is to be conveyed.

SUMMARY OF THE INVENTION

The present invention relates to an article having an identification mark that combines many of the advantages of both the ink printing and laser engraving technologies described above, with the result that the identification mark is aesthetic, easy to read and relatively inexpensive. The identification mark of the present invention can be tailor-made as needed to create specific data for specific products with little human intervention. The present invention is also directed toward a method for making the improved identification mark.

In one aspect, the present invention is directed toward an article that comprises a body having an exterior surface with a certain color. A polymer coating extends over a certain region of the exterior surface. The coating has a color that contrasts with the color of the exterior surface. The article also includes a laser engraved identification mark that is formed within the coating.

Another aspect of the present invention is directed toward a method of making an article. The method includes the act of selecting a polymer coating having a color that contrasts with the color of an exterior surface of the article. The method also includes the act of applying the coating to a certain region of the exterior surface of the article. The method further includes the act of directing a laser beam toward the coating with sufficient power to cause the coating to undergo a chemical reaction and create an identification mark.

These and other aspects of the invention are described in more detail below and are illustrated in the accompanying drawings.

DETAILED DESCRIPTION OF THE PREFERRED EMBODIMENTS

Figure 1:
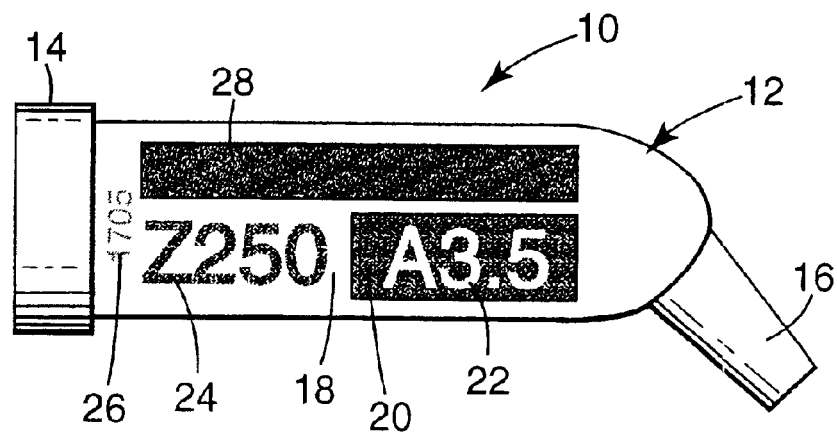
FIG. 1 is a side elevational view of an article having a laser engraved identification mark according to one embodiment of the present invention, where the article in this instance is a product container and specifically is a disposable cartridge for storing and dispensing a quantity of dental material.

An article having a laser engraved identification mark according to one embodiment of the invention is illustrated in FIG. 1 and is a product container that is broadly designated by the numeral 10. The product container 10 in this example is a disposable cartridge for storing and containing a flowable material. More particularly, the product container 10 shown in FIG. 1 is a disposable storage and dispensing cartridge for use with a single dental patient and is especially useful for storing and containing dental compositions such as dental sealant or dental restorative material.

The product container 10 includes a body 12 that is optionally made of a polymeric material. The body includes a circular rear flange 14 and a front dispensing nozzle 16. Although not shown in the drawing, the body 12 has a hollow inner chamber for containing a material to be dispensed. Additionally, the product container 10 includes a piston that is received within the chamber. As the piston is advanced toward the nozzle 16, the material in the chamber is urged through a passageway in the nozzle 16 and dispensed directly to an application site. Additional aspects of the container 10 are described in U.S. Pat. Nos. 5,100,320 and 5,624,260, both of which are incorporated by reference herein.

The particular product container 10 that is depicted in FIG. 1 is shown only for exemplary purposes, and a number of other containers are also possible. For example, the container may have any one of a number of other shapes or sizes, and may be used to contain material other than a dental sealant or restorative material. The container may also optionally have multiple product chambers, such as the double-barrel cartridge shown in U.S. Pat. Nos. 5,722,829 and 5,651,397.

The container 10 is adapted to be releasably received in a receptacle of a hand-held applicator, such as the applicators described in U.S. Pat. Nos. 5,195,663 and 4,198,756. However, other constructions are also possible. For example, the container may include applicator structure for hand dispensing of the material, such as the dispenser assembly with integral containers shown in U.S. Pat. No. 5,735,437.

The body 12 has an exterior surface 18 with a certain color. A section of polymer coating 20 extends over a certain region of the exterior surface 18. The area of the region is less than the area of the entire exterior surface 18. In this embodiment, that region has a rectangular shape, although other shapes are also possible. Preferably, the coating 20 has a color that contrasts with the color of the exterior surface 18, such that the coating 20 can be readily distinguished from the exterior surface 18 by the naked eye.

The article or product container 10 also includes a laser engraved identification mark 22 that is formed within the coating 20 and extends over the above-mentioned rectangular region of the exterior surface 18. In FIG. 1, the identification mark 22 bears the alphanumeric designation "A3.5" for purposes of illustration. The identification mark 22 is of a color that is different than the color of the adjacent area of the coating 20, so that it is relatively easy to see.

The identification mark 22 is formed by directing a laser beam toward the polymer coating and causing a portion of the coating to undergo a chemical reaction and form a desired identifying designation. For example, the laser beam can be directed toward the coating with sufficient power to volatilize the portion of the coating that is in the path of the laser beam. The laser beam is then moved as needed to create the desired alphabetic, numeric or other type(s) of identification mark(s). In the illustrated embodiment, the portion of the coating within the desired area of the identification mark is essentially completely volatilized so that the exterior surface 18 is readily visible and contrasts with adjacent areas of the coating 20.

Optionally, the coating 20 also presents a second identification mark. An example of one type of second identification mark is the identification mark 24 that bears the alphanumeric designation "Z250". The second identification mark 24 is located in an area on the exterior surface 18 that is spaced from the rectangular region containing the identification mark 22.

Preferably, the second identification mark 24 is a genus identification mark, while the first identification mark 22 is a species identification mark. For example, the identification mark 24 may be used to identify a series of dental restorative materials that have identical physical characteristics except for color or shade. The first identification mark 22 may then be used to designate a shade of the dental restorative material, so that a restorative material can be selected that matches the shade of the patient's tooth structure.

The product container 10 that is shown in FIG. 1 is a particular advantage, in that a number of such containers 10 may be manufactured in advance bearing the second identification mark 24 but not the first identification mark 22. As the containers 10 are taken out of inventory by the manufacturer and filled when needed with a particular shade of restorative material, the laser apparatus can be used to create the first identification mark 22 and permanently mark the product container 10 with a shade designation that identifies the particular shade of dental restorative material in the chamber of the product container 10. As such, a manufacturer need only keep in inventory one type of product container for each product series (e.g., "Z250"), instead of keeping a number of different product containers to identify all of the different types of products (e.g., the various shades) within that series.

Optionally, the coating 20 may have a color that represents a non-laser engraved genus identification mark. For example, the coating may have a red color for use with a product container having a black exterior surface to represent one series of dental restorative materials especially suitable for use with posterior teeth, while the coating may have a green color for use with a product container having a black exterior surface to represent another product series of restorative materials that is especially suitable for use with anterior teeth. The first identification mark 22 can then be used to create the species identification mark that identifies the color or shade of the restorative material within each of those series.

As another option, the shape of the coating 20 may represent a genus identification mark. For example, the shape of the coating 20 over the exterior surface 18 may be rectangular (as illustrated) to represent one series of products, and may be triangular or round to represent another series of products. Other variations are also possible.

As another option, the laser beam may cause the coating to undergo a chemical reaction other than volatilization. For example, the laser beam may cause the coating in its path to oxidize, such that the surface oxides contrast in color with the color of the adjacent coating. As another example, the laser beam may cause the coating in its path to harden and/or cure and become affixed to the container, while the remainder of the coating is subsequently removed by a rinsing or dissolving step. As a further example, the laser beam may cause the coating to undergo a color removal (photobleaching) process or a color generation process that contrasts in color with adjacent areas of the coating. Other types of chemical reactions caused by the laser beam are also possible. Moreover, all of the processes described in this paragraph shall be considered for present purposes as forming a laser engraved identification mark "within the coating", regardless of whether the resulting mark is a negative or a positive image.

The use of a polymer coating in combination with a laser engraving process is a particular advantage in certain instances where it is desired that the laser beam not disturb the exterior surface to any significant degree. For example, there may be instances where it is desired to avoid any surface irregularities on the article (as, for example, when it is desired to limit potential corrosion sites on metal articles). In other instances, the article may be made of a material that might be unduly weakened by the laser beam. In these instances, the presence of the coating optionally enables the coating instead of the underlying exterior surface of the body to receive a majority of the energy of the laser beam, so that the underlying surface of the body is not adversely affected. However, if desired in certain applications, the laser beam may be directed at the article with sufficient energy to roughen the exterior surface of the article and also optionally enable the coating to "settle in" to the roughened portions and form the desired identification mark.

As another option, the laser beam may also be used to create a third identification mark having a different purpose than the first identification mark 22 or the second identification mark 24. The third identification mark 26 may be made directly on the exterior surface 18 in a location that is spaced from the coating, resulting in a mark that is more difficult to see with the naked eye than the first identification mark 22 or the second identification mark 24. The third identification mark is particularly useful to record information directly on the product container 10 that need not be known or observed by the consumer in ordinary use of the product.

For example, the third identification mark 26 may contain a lot code or batch code. Although such codes are not normally needed, they are often permanently marked on containers to aid in tracing the product when necessary. For instance, if the manufacturer needs to recall all material made in a certain batch or in a certain lot, the lot or batch code can be identified when desired by the naked eye so that the consumer can ascertain whether or not the product within the product container 10 is subject to the recall.

As additional alternatives, the third identification mark 26 may include data such as a recommended use date, recommended sell date, shelf life data, expiration date or date of manufacture of the product in the product container 10. Such information may not be needed in the ordinary course of practice, as for example in a busy dental office where new products arrive at frequent intervals. However, the practitioner can refer to the third identification mark 26 to obtain such information upon closer inspection when needed or desired.

The coating 20, including the rectangular section as well as the second identification mark 24, may be made by any one of a number of suitable ink printing techniques. For example, the coating may be applied to the exterior surface 18 by a pad printing machine. If desired, both the rectangular section of the coating as well as the second identification mark may be applied simultaneously in a single step by the pad printing machine. Examples of suitable pad printing machines are the machines sold by Printex (a division of Pemco Industries, Inc.) of Poway, Calif. Alternatively, the coating 20 may be applied by a screen printing technique. As another alternative, the coating 20 may be applied to the body 12 by use of an in-mold decorating technique, where a web containing the polymer is present in the mold cavity as the body 12 is molded.

The polymer coating may be any suitable coating that is compatible with the selected laser engraving system and the composition of the exterior surface 18. Examples of suitable coatings are the inks known as the "PUR" Series, from Purell of Germany or the inks known as "Visprox" from Visprox B.V.

The laser engraved first identification mark 22 may be made using any one of a number of laser engraving systems. An example of a suitable laser engraving system is a YAG laser engraving system sold under the brand name "Hi-Mark" No. 400 from General Scanning Inc. However, other laser systems such as $CO_2$ lasers and masers may also be employed. The third identification mark 24, if used, is preferably applied to the product container 10 by the same system used to create the first identification mark 22.

The laser engraving system is adjusted as needed so that the resulting identification mark 22 is readily visible. For example, when the "PUR" Series ink as described above is used in combination with the "Hi-Mark" brand laser marking system No. 400 as mentioned above, and when the body 12 is made of nylon, satisfactory settings for the laser engraving system include a speed of 70 mm per second, a power setting of 80% and a frequency of 30,000 Hertz.

The identification mark 22 may be made using one or two passes of the laser beam, or additional passes if a somewhat wider mark is desired. In some instances, at least two passes of the laser beam are desirable so that the energy of the beam can be retained at relatively low levels that do not tend to unduly soften the exterior surface 18 of the underlying plastic body 12. The use of multiple parallel beam paths also helps avoid the need to use a zoom lens or beam expander with the laser apparatus, resulting in a potential cost savings.

Preferably, the settings of the laser engraving system are selected so that the polymer coating in the path of the beam is volatilized but the underlying exterior surface of the body 12 is not unduly heated or softened. It has been found that a laser beam with excess energy may soften the exterior surface 18 of the body 12 to such an extent that the plastic material of the exterior surface 12 tends to roll over edges of the coating on a microscopic scale, causing the edges of the coating to lose sharpness and become somewhat fuzzy in appearance. By keeping the energy of the laser beam as low as possible while still volatilizing the coating in the path of the beam, the edges, of the coating adjacent the path of the beam are sharp and distinct, resulting in an identification mark that is relatively easy to read.

As an additional option, the container 10 may have an area 28 that is color coded to certain information conveyed by the identification mark 22 or identification mark 24. For example, the containers for the product series "Z250" identified by the second mark 24 may have a common color in the area 28, so that the risk of using the wrong product for a particular procedure is reduced.

Figure 2:
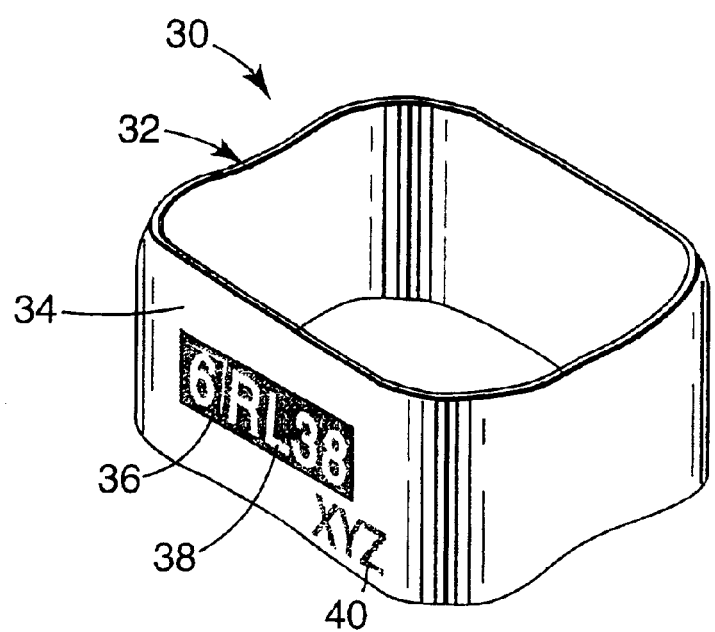
FIG. 2 is a perspective view of an article with a laser engraved identification mark according to another aspect of the invention, where the article in this instance is an orthodontic band.

A laser engraved article according to another embodiment of the invention is illustrated in FIG. 2. The article in FIG. 2 is an orthodontic band 30. Orthodontic bands are commonly placed over molar teeth of a patient undergoing orthodontic treatment to serve as a mounting platform for tiny devices known as buccal tubes.

The orthodontic band 30 includes a circular body 22 that is made of a metallic material such as Series 300 stainless steel. The body 32 has an exterior surface 34. A polymer coating 36 is applied to a region of the exterior surface 34.

A laser engraved first identification mark 38 is formed by directing a laser beam toward the polymer coating 36, such that the portion of the coating 36 that is within the path of the laser beam undergoes a chemical reaction. Preferably, the chemical reaction volatilizes the coating in the path of the laser beam, so that an identification mark is formed by the appearance of the exterior surface beneath the area where the polymer coating 36 is volatilized. Preferably, and as described above, the laser engraving system is operated so that the exterior surface 34 is not unduly roughened or otherwise disturbed by the laser beam.

The first identification mark 38 is preferably located on a portion of the body 32 where the identification mark 38 is not normally visible once the band 30 is placed in the patient's oral cavity and around the selected tooth. For example, the identification mark 38 may be positioned on a mesial side of the molar tooth in interproximal relation to the adjacent tooth when the band 30 is placed over the tooth in its correct orientation.

Preferably, the polymer coating 36 is not adversely affected when the band 30 is subject to sterilization. Orthodontic bands are available in a variety of shapes and sizes, and the orthodontic practitioner may trial fit the band over the patient's tooth before the band is cemented in place to ensure that the selected band matches the shape of the patient's tooth. If the band is not of the proper size, the band is re-sterilized for later use. It is preferable that the polymer coating 36 be able to withstand the sterilization procedure so that the identification mark 38 remains easy to read during a subsequent procedure.

Optionally, the band 30 also includes a second identification mark 40 that represents genus data, while the first identification mark 38 represents species data For example, the first identification mark 38 may include numerals sufficient to identify the location of the tooth for which the band 30 is intended. The identification mark 38 may also include a manufacturer's notation that represents a size of the band 30. The second identification mark 40 may be used to provide more generic information such as the brand name of the band or the identity of the manufacturer. In the illustrated example, the second identification mark 40 identified the brand name as "XYZ".

A number of other laser engraved articles are also possible, and the embodiments described in detail above are only representative of specific examples. Those skilled in the art may recognize a variety of other applications and uses of the invention. Accordingly, the invention should not be deemed limited to the specific embodiments that are described above, but instead only by a fair scope of the claims that follow along with their equivalents.

What is claimed is:

1. A set of articles, each article comprising:
   a product container having a polymeric body and a chamber within the body, each body having an exterior surface with a certain color, wherein the product container includes a flowable material within the chamber, and wherein the flowable material is a dental sealant or a dental restorative material;
   a polymer coating extending over the exterior surface, the coating having a color that contrasts with the color of the exterior surface, the coating including a certain region and also a certain area that is spaced from the certain region, the polymer coating presenting a non-laser engraved genus identification mark in the certain area; and
   a laser engraved identification mark formed within the certain region of the coating, the laser engraved identification mark being a species mark.

2. A set of articles according to claim 1 wherein the exterior surface of at least one article is visible within the species identification mark.

3. A set of articles according to claim 2 wherein the exterior surface visible within the species identification mark of at least one article is devoid of surface irregularities.

4. A set of articles according to claim 1 wherein the laser engraved identification mark of at least one article has a color that is different than the color of the polymer coating.

5. A set of articles according to claim 1 wherein the polymer coating of at least one article has a color presenting the genus identification mark.

6. A set of articles according to claim 1 wherein the color of the polymer coating matches the color of the dental material.

7. A set of articles according to claim 1 wherein at least one article also includes a laser engraved identification mark that is spaced apart from the region of the exterior surface and is more difficult to see than the laser engraved identification mark formed within the certain region.

8. A set of articles according to claim 7 wherein the laser engraved identification mark that is spaced apart from the region of the exterior surface includes information selected from a group consisting of shelf life data, expiration data, date of manufacture, serial number, batch code data and lot code data.

9. A set of articles, each article comprising:
   a body having an exterior surface with a certain color;
   a polymer coating extending over the exterior surface, the coating having a color that contrasts with tho color of the exterior surface, the coating including a certain region and also a certain area that is spaced from the certain region, the polymer coating presenting a non-laser engraved genus identification mark in the certain area; and
   a laser engraved identification mark formed within the certain region of the coating, the laser engraved identification mark being a species mark, wherein the polymer coating of at least one article has a color presenting the genus identification mark, wherein at least one article includes a container and a product in the container, and wherein the color of the polymer coating of the at least one article matches the color of the product.

10. A set of articles according to claim 9 wherein the product is a dental sealant or a dental restorative material.

11. A set of articles comprising at least a first series and a second series, each article comprising:

a body having an exterior surface with a certain color;

a polymer coating extending over the exterior surface, the coating having a color that contrasts with the color of the exterior surface, the coating including a certain region and also a certain area that is spaced from the certain region, the color of the polymer coating presenting a non-laser engraved genus identification mark in the certain area; and a laser engraved identification mark formed within the certain region of the coating, the laser engraved identification mark being a species mark, wherein at least one article of the first series includes a container and a product in the container, wherein at least one article of the second series includes a container and a product in the container that is different than the product in the container of the first series, wherein the color of the coating of the articles of the second series is different than the color of the coating of the articles of the first series, wherein the product in the container of at least one article of the first series is a dental material that is especially suitable for use with certain teeth, and wherein the product in the container of at least one article of the second series is a dental material that is especially suitable for use with teeth other than the certain teeth.

12. A set of articles, each article comprising:

a body having an exterior surface with a certain color;

a polymer coating extending over the exterior surface, the coating having a color that contrasts with the color of the exterior surface, the coating including a certain region and also a certain area that is spaced from the certain region, the polymer coating presenting a non-laser engraved genus identification mark in tho certain area; and a laser engraved identification mark formed within the certain region of the coating, the laser engraved identification mark being a species mark, wherein at least one article is an orthodontic band.

13. A method of marking a set of articles comprising the acts of:

selecting a polymer coating having a color that contrasts with the color of an exterior surface of each article;

applying the coating to a certain region of the exterior surface of each article; and directing a laser beam toward the coating with sufficient power to cause at least a portion of the coating to undergo a chemical reaction and create an identification mark, wherein the act of directing the laser beam toward the coating creates a species mark, and wherein the act of applying the coating to the exterior surface of the article includes the act of creating a non-laser engraved genus mark that is distinct from the species mark, wherein at least one article comprises a container made of a polymeric material and wherein the act of directing a laser beam toward the coating does not substantially soften the exterior surface of the container, and wherein the container includes a chamber and a dental sealant or dental restorative material within the chamber.

14. A method of marking a set of articles according to claim 13 wherein the act of directing a laser beam toward the coating causes at least some of the coating to volatilize.

15. A method of marking a set of articles according to claim 14 wherein the act of directing a laser beam toward the coating does not cause any sure irregularity on the exterior surface of at least one article.

16. A method of marking a set of articles according to claim 13 wherein the act of directing a laser beam toward the coating causes at least some of the coating to polymerize.

17. A method of marking a act of articles according to claim 13 wherein the act of directing a laser beam toward the coating does not cause any substantial amount of surface irregularities on the exterior surface of the article.

18. A method of marking a set of articles according to claim 13 wherein the act of directing a laser beam toward the coating causes at least some of the coating to change color.

19. A method of marking a set of articles according to claim 18 wherein the act of directing a laser beam toward the coating does not cause any substantial amount of surface irregularities on the exterior surface of at least one article.

20. A method of marking a set of articles according to claim 13 wherein the act of creating a genus mark includes the act of selecting a color of the polymer coating.

21. A method of marking a set of articles according to claim 13 wherein the act of creating the genus mark is carried out for all of the articles in the set before the act of directing a laser beam toward the coating is carried out for any article of the set.

22. A method of marking a set of articles comprising the acts of:

selecting a polymer coating having a color that contrasts with the color of an exterior surface of each article;

applying the coating to a certain region of the exterior surface of each article; and directing a laser beam toward the coating with sufficient power to cause at least a portion of the coating to undergo a chemical reaction and create an identification mark, wherein the act of directing the laser beam toward the coating creates a species mark, and wherein the act of applying the coating to the exterior surface of the article includes the act of creating a non-laser engraved genus mark that is distinct from the species mark, wherein at least one article comprises a container and a product in the container, and wherein the act of selecting a polymer coating includes the act of selecting a polymer coating that has a color matching the color of the product in the container.

23. A method of marking a set of articles according to claim 22 wherein the product is a dental sealant or dental restorative material.

24. A method of marking a set of articles according to claim 13 and including the act of directing the laser beam toward at least one article at a location spaced from the costing in order to create another identification mark.

25. A method of marking a set of articles according to claim 24 wherein the act of directing the laser beam toward at least one article at a location spaced from the coating creates an identification mark that is more difficult to see than the identification mark that is created by the act of directing a laser beam toward the coating.

26. A method of marking a set of articles comprising the acts of:

selecting a polymer coating having a color that contrasts with the color of an exterior surface of each article;

applying the coating to a certain region of the exterior surface of each article; and directing a laser beam toward the coating with sufficient power to cause at least a portion of the coating to undergo a chemical reaction and create an identification mark, wherein the act of directing the laser beam toward the coating creates a species mark, and wherein the act of applying the coating to the exterior surface of the article includes the act of creating a non-laser engraved genus mark that is distinct from the species mark, wherein at least one article is an orthodontic band.

* * * * *

UNITED STATES PATENT AND TRADEMARK OFFICE
CERTIFICATE OF CORRECTION

PATENT NO. : 6,780,012 B1  Page 1 of 1
DATED : August 24, 2004
INVENTOR(S) : Peterson, Dale D.

It is certified that error appears in the above-identified patent and that said Letters Patent is hereby corrected as shown below:

Column 2,
Line 41, after "manufacture" delete ",".

Column 7,
Line 7, after "edges" delete ",".

Column 8,
Line 59, delete "tho" and insert -- the --, therefor.

Column 9,
Line 44, delete "tho" and insert -- the --, therefor.

Column 10,
Line 10, delete "sure" and insert -- surface --, therefor.
Line 15, delete "act" and insert -- set --, therefor.

Signed and Sealed this

Sixteenth Day of November, 2004

JON W. DUDAS
*Director of the United States Patent and Trademark Office*